(12) United States Patent
Brekke

(10) Patent No.: US 8,997,555 B2
(45) Date of Patent: Apr. 7, 2015

(54) SYSTEM AND METHOD FOR GENERATING A CHANGE IN PRESSURE PROPORTIONAL TO FLUID VISCOSITY

(71) Applicant: Kristian Brekke, Bellaire, TX (US)

(72) Inventor: Kristian Brekke, Bellaire, TX (US)

(73) Assignee: Flowpro Well Technology a.s., Oslo (NO)

( * ) Notice: Subject to any disclaimer, the term of this patent is extended or adjusted under 35 U.S.C. 154(b) by 255 days.

(21) Appl. No.: 13/735,258

(22) Filed: Jan. 7, 2013

(65) Prior Publication Data

US 2014/0190573 A1  Jul. 10, 2014

(51) Int. Cl.
| | |
|---|---|
| *G01N 11/02* | (2006.01) |
| *G01N 11/04* | (2006.01) |
| *G05D 16/14* | (2006.01) |
| *F17D 1/14* | (2006.01) |
| *G01N 11/00* | (2006.01) |
| *G01N 11/08* | (2006.01) |

(52) U.S. Cl.
CPC ...... *G05D 16/14* (2013.01); *F17D 1/14* (2013.01); *G01N 11/00* (2013.01); *G01N 11/02* (2013.01); *G01N 11/04* (2013.01); *G01N 11/08* (2013.01)

(58) Field of Classification Search
CPC ........... G01L 7/00; G01L 7/084; G01L 13/00; G01L 13/02; G01L 13/023; G01L 13/025; G01L 13/026; G01L 15/00; G01L 19/0007

USPC .......... 73/53.01, 54.01, 54.04, 54.05, 54.06, 73/54.09
See application file for complete search history.

(56) References Cited

U.S. PATENT DOCUMENTS

| | | | | |
|---|---|---|---|---|
| 7,784,330 | B2 * | 8/2010 | Angelescu et al. | 73/54.09 |
| 2010/0191481 | A1 * | 7/2010 | Steven | 702/47 |
| 2011/0028354 | A1 * | 2/2011 | Le et al. | 507/211 |
| 2011/0029259 | A1 * | 2/2011 | Cunningham et al. | 702/47 |
| 2011/0301867 | A1 * | 12/2011 | Davis et al. | 702/30 |

* cited by examiner

*Primary Examiner* — David A Rogers
(74) *Attorney, Agent, or Firm* — Spradley PLLC; Michael Spradley

(57) ABSTRACT

A system and method for generating a change in pressure proportional to fluid viscosity is disclosed herein. The system can comprise a first pilot stream, a second pilot stream, and a pressure sensing device that reads a differential pressure across a first junction on the first pilot stream and a second junction on the second pilot stream. The first junction is between a first section having a first predominant pressure loss characteristic, and a second section having a second predominant pressure loss characteristic. Similarly, the second junction can be between a third section having a third predominant pressure loss characteristic and a fourth section having a fourth pressure loss characteristic.

12 Claims, 3 Drawing Sheets

SYSTEM AND METHOD FOR GENERATING A CHANGE IN PRESSURE PROPORTIONAL TO FLUID VISCOSITY

BACKGROUND

This disclosure relates to a system and method for generating a change in pressure proportional to fluid viscosity. This disclosure further relates to how change in pressure can be used to control a system according to the viscosity of material flowing within a system. For purposes of this disclosure, various embodiments are discussed, and are examples of a system and method for generating a change in pressure proportional to viscosity. However, such discussion of these embodiments is solely exemplary, and not limiting.

Control systems and methods of controlling process and flow systems have changed significantly over time, tending toward automated control in lieu of manual control. Examples of evolution in control systems include many kinds of switches based on everything from pressure, temperature, or liquid levels, to automated valves controllable by programmable logic controller. In short, the current tendency is for control systems to be able to recognize attributes of its system to adapt to changing operating conditions.

Today, one problem facing downhole hydrocarbon evacuation is regulating inflow of oil, water, and gas phases in oil and gas well completions or for separation of different phases of a fluid stream. Typically, different viscosities will be associated with different phases in a fluid stream, however the pressure of the stream will largely be unaffected by changes in viscosity. For this reason, pressure switches connected with automated valves have not been directly useful for separating or controlling flow based on phase or material.

As such it would be useful to have an improved system and method for generating a change in pressure proportional to fluid viscosity.

SUMMARY

This disclosure relates to a system and method for generating a change in pressure proportional to fluid viscosity. In particular, the disclosure discusses a viscosity dependent pressure differential system. The system can comprise a first pilot stream, a second pilot stream, and a pressure sensing device that reads a differential pressure across a first junction on the first pilot stream and a second junction on the second pilot stream. The first junction is between a first section having a first predominant pressure loss characteristic, and a second section having a second predominant pressure loss characteristic. Similarly, the second junction can be between a third section having a third predominant pressure loss characteristic and a fourth section having a fourth pressure loss characteristic.

Additionally, the disclosure discusses a method for determining viscosity using differential pressure. The method can comprise the step of measuring a differential pressure between a first junction and a second junction. The first junction is between a first pilot stream first section having a first predominant pressure loss characteristic, and a second section having a second predominant pressure loss characteristic. The second junction between a second pilot stream first section having a third predominant pressure loss characteristic and a second pilot stream second section having a fourth predominant pressure loss characteristic.

DETAILED DESCRIPTION

Described herein is a system and method for generating a change in pressure proportional to fluid viscosity. The following description is presented to enable any person skilled in the art to make and use the invention as claimed and is provided in the context of the particular examples discussed below, variations of which will be readily apparent to those skilled in the art. In the interest of clarity, not all features of an actual implementation are described in this specification. It will be appreciated that in the development of any such actual implementation (as in any development project), design decisions must be made to achieve the designers' specific goals (e.g., compliance with system- and business-related constraints), and that these goals will vary from one implementation to another. It will also be appreciated that such development effort might be complex and time-consuming, but would nevertheless be a routine undertaking for those of ordinary skill in the field of the appropriate art having the benefit of this disclosure. Accordingly, the claims appended hereto are not intended to be limited by the disclosed embodiments, but are to be accorded their widest scope consistent with the principles and features disclosed herein.

Figure 1:
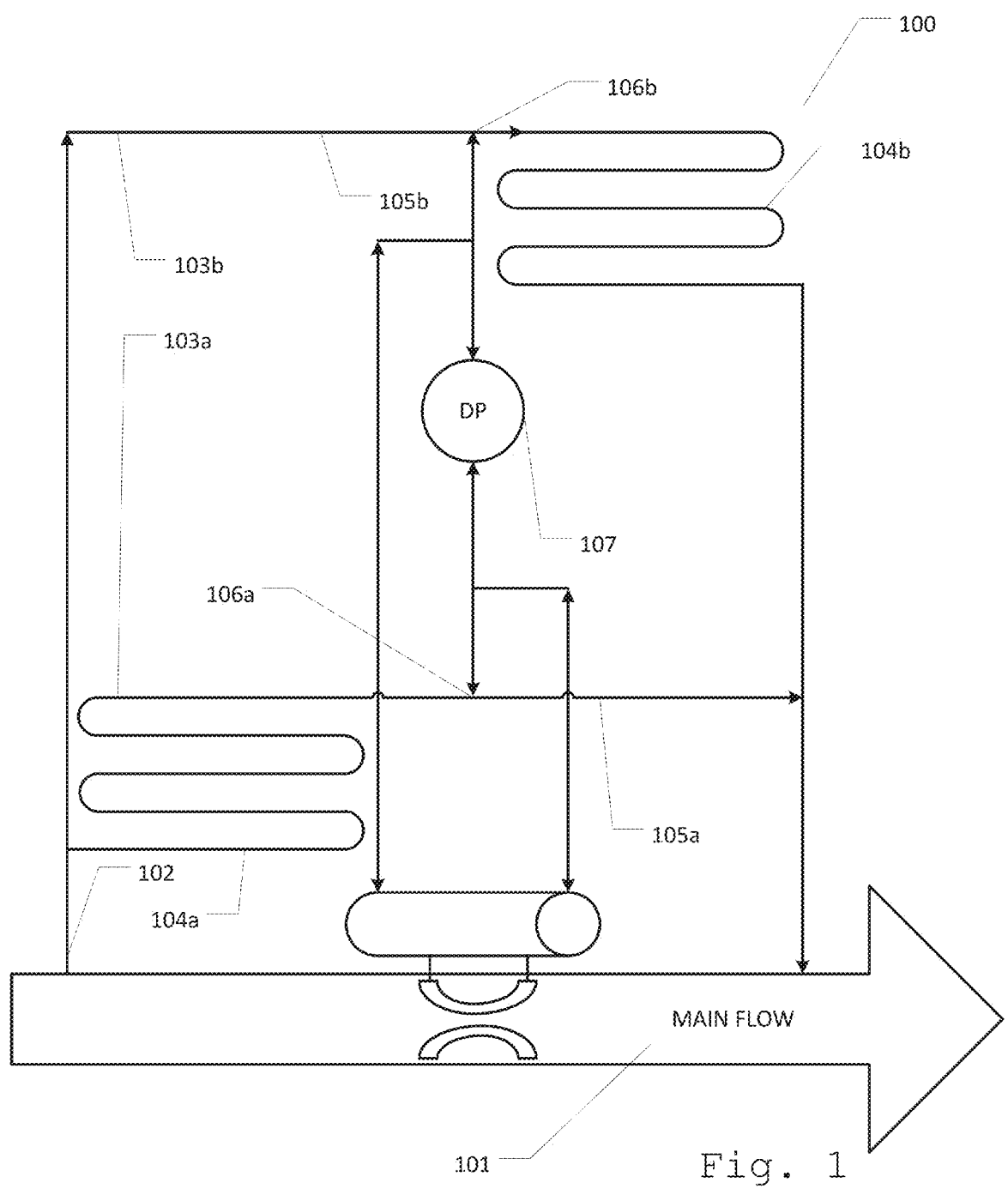
FIG. 1 illustrates a system for generating a change in pressure proportional to fluid viscosity.

FIG. 1 illustrates an exemplary velocity dependent pressure differential (VDPD) system 100 connected to a pipeline with a main stream 101 flowing through it. In one embodiment, VDPD system 100 can comprise a pre-pilot stream 102 side tracked from mainstream 101 through a pre-pilot pipeline. In said embodiment, pre-pilot stream 102 can divide into multiple pilot stream pipelines each with a pilot stream 103, as shown in FIG. 1 as pilot stream 103a and pilot stream 103b. In another embodiment, two or more pilot streams can come directly off main stream 101, with no pre-pilot stream 102. In another embodiment, main stream 101 can divide into two or more pilot streams 103.

Pilot stream 103a can follow two flow paths, an inertia altering path 104a, and a frictional path 105a, connected to form one complete path. Inertia altering path 104a and frictional path 105a can be connected at a junction 106a. Pilot stream 103a first passes through inertia altering path 104a, and then through frictional path 105a. Pilot stream 103b also follow two flow paths, inertia altering path 104b, and frictional path 105b, connected to form one complete path. Inertia altering path 104b and frictional path 105b are connected at a junction 106b. Pilot stream 103b first passes through frictional path 105b, and then through inertia altering path 104b.

In general, as fluid flows through a path, it can experience pressure loss for varying reasons. Types of pressure loss include hydrostatic pressure loss, frictional pressure loss, and inertial pressure loss. Hydrostatic pressure loss and inertial pressure loss depend primarily on fluid density, and can vary depending on the geometric shape of a flow path. For example, a flow path that experiences a change in elevation will experience hydrostatic pressure losses. Additionally, directional changes or an abrupt narrowing of the flow path such as an orifice cause inertial pressure losses. Frictional pressure loss, however results from the wall shear, and depends heavily on fluid viscosity. Because of these differences, a system and method that can isolate frictional pressure loss from the other types of pressure loss can be used to relate the viscosity of a material to a differential pressure reading.

Relating this information to the example in FIG. 1, as pilot stream 103a follows inertia altering path 104a, pilot stream 103a will experience a high level of inertial pressure loss between the pilot split point and junction 106a.

Next, as pilot stream 103a follows frictional path 105a, pilot stream 103a experiences predominantly frictional pressure loss. Similarly, but in reverse order, as pilot stream 103b follows frictional path 105b, pilot stream 103b will experience predominantly frictional pressure loss between the pilot split point and junction 106b. Next, as pilot stream 103b follows inertia altering path 104b, pilot stream 103b experiences a high level of inertia pressure loss. The total pressure loss by pilot stream 103b will be substantially equal to the total pressure loss by pilot stream 103a as long as inertia altering path 104a and inertia altering path 104b are the same, and frictional path 105a and frictional path 105b are the same. However, between junction 106a and junction 106b, there will be a pressure differential. The pressure differential will vary depending on the viscosity of the material. In one embodiment the pressure differential between points 106a and 106b inside the flow path can be measured directly by a differential pressure sensor, which can be inside pilot stream 103. In another embodiment the pressure differential can be measured through the wall of pilot stream 103. However, the way in which pressure is measured is not limiting to this disclosure.

For VDPD system 100, a particular fluid viscosity can yield a pressure deferential, measured by a pressure sensing device 107, that is zero. For expedience, such viscosity will hereinafter be referred to as $V_0$. In another VDPD system 100, $V_0$ can be a positive or negative pressure differential. Materials with a viscosity greater than $V_0$ will yield pressure differential greater than $V_0$. Such pressure differential shall be referred to as $V_+$. Materials with a viscosity less than $V_0$ will yield pressure differential less than $V_0$. Such pressure differential can be referred to as $V_-$. By changing the characteristics of the system, for example, the size of an orifice or the length of straight pipe, a VDPD system 100 designer can adjust the $V_0$.

In one scenario, main stream 101 could have on occasion one of two known chemicals, chemical A or chemical B, passing through it at anytime. However, at any point in time, what chemical is passing through is not readily or immediately knowable by a system operator. Such pressure differential can determine in real-time what is passing through main stream 101. As both chemicals are known, an operator can know the viscosity of chemical A and the viscosity of chemical B, referred to as $V_A$ and $V_B$, respectively. Assuming $V_A > V_B$, Operator can adjust VDPD system 100 such that $V_B < V_0 < V_A$. In such system, $V_A$ will be a $V_+$, and $V_B$ will be a $V_-$. That is to say that chemical A can yield differential pressure 107 greater than $V_0$ in VDPD system 100 as it flows through main stream 101, and chemical B can yield differential pressure 107 less than $V_0$ in VDPD system 100 as it flows through main stream 101.

Once viscosity information is determined at a system level, controls to flow and other system processes can be made based on the viscosity information using pressure-controlled actuators commonly known in the art. In FIG. 1, VDPD system 100 can connect to a pressure controlled flow valve controlling the flow of main stream 101.

Figure 2:
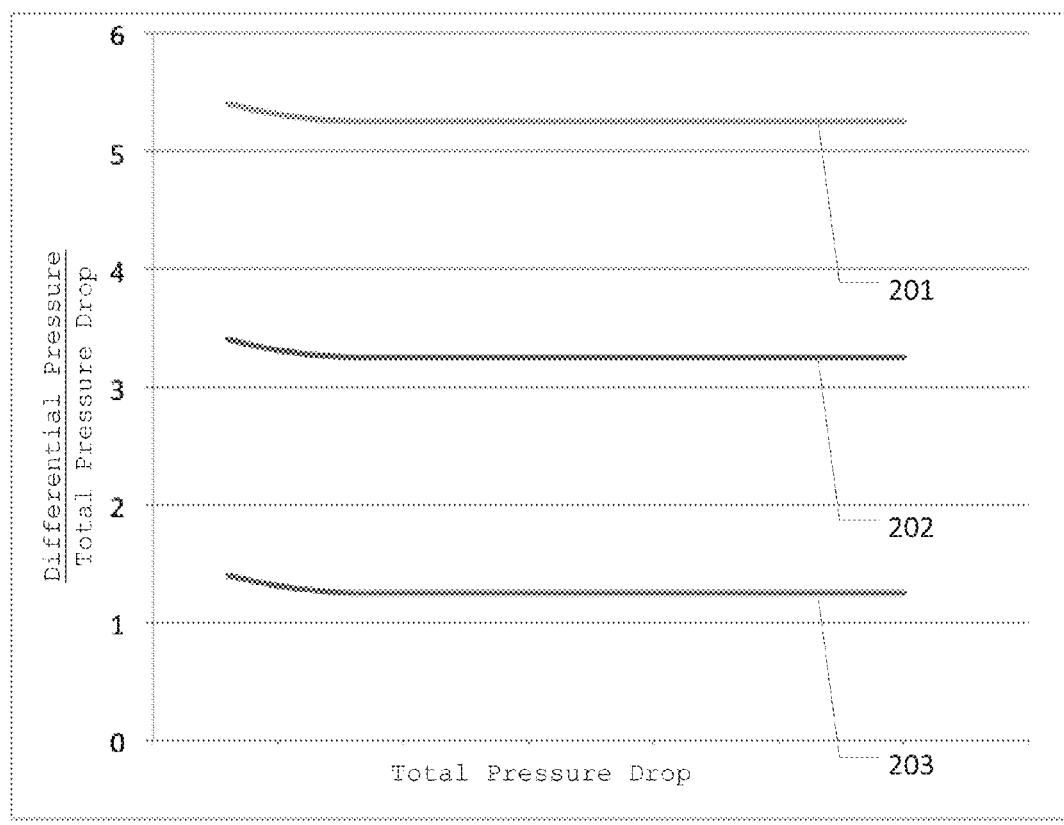
FIG. 2 illustrates a graph displaying the ratio of the pressure differential between junctions 106a and 106b over total pressure loss (y-axis), to the total pressure loss across the pilot loop (x-axis) for various materials.

FIG. 2 illustrates a graph displaying the ratio of the pressure differential between junctions 106a and 106b over total pressure loss (x-axis), to total pressure loss across the pilot loop (x-axis), for $V_-$ 201, $V_0$ 202, and $V_+$ 203. This ratio can also be a strong function of viscosity, and weak function of total pressure loss, as seen in FIG. 2. Thus, the ratio of pressure differential between junctions to total pressure differentials across streams can be used as a measure of viscosity over a range of total pressure differentials across streams. By knowing characteristics of VDPD system 100 along with pressure differentials, an operator and/or intelligent system can know the viscosity and therefore the material flowing through the pipeline.

Figure 3:
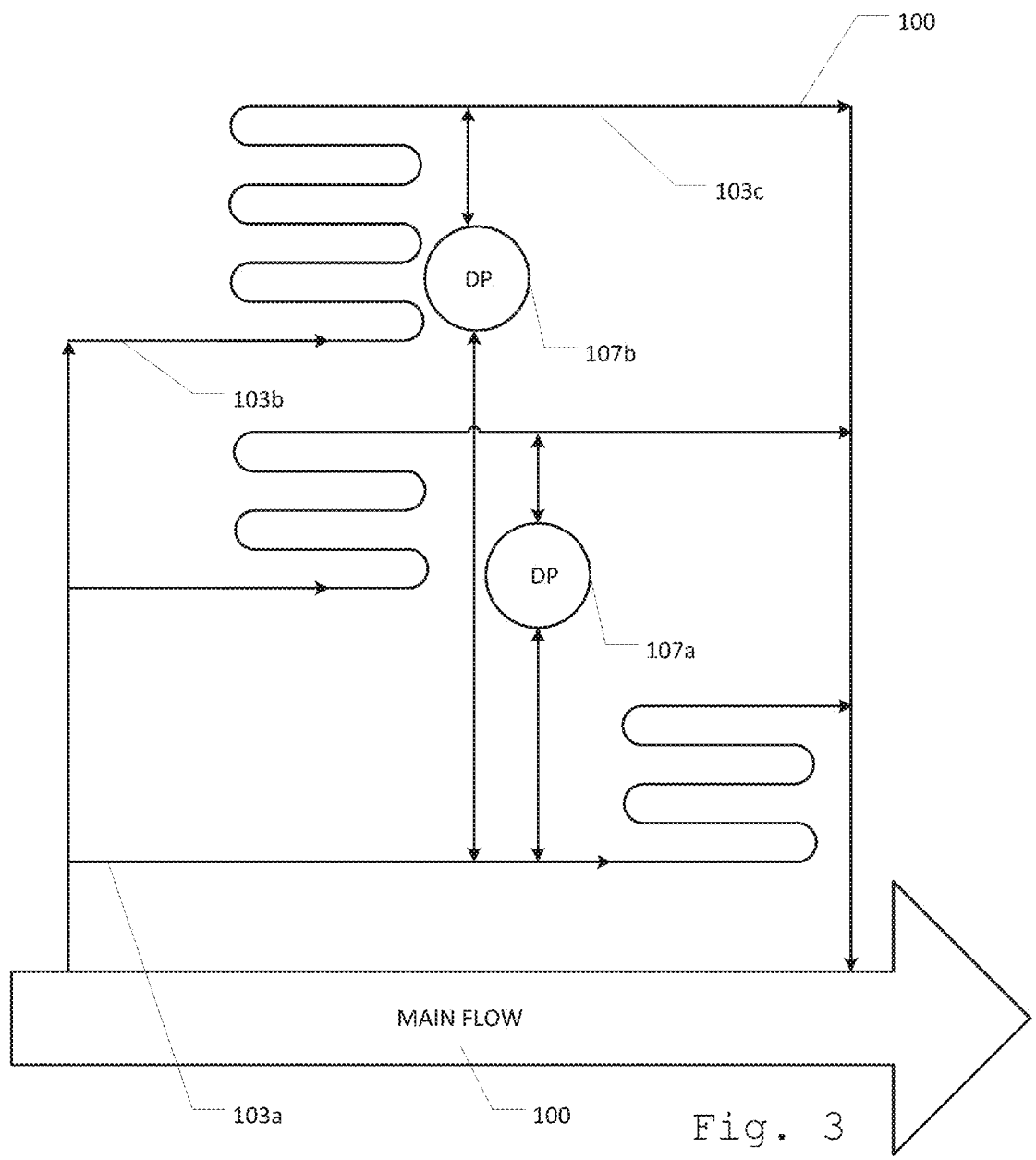
FIG. 3 illustrates a VDPD system comprising multiple pressure differentials, $V_{0-1}$ and $V_{0-2}$ measured by a first pressure sensing device and a second pressure sensing device.

FIG. 3 illustrates a VDPD system 100 comprising multiple pressure differentials, $V_{0-1}$ and $V_{0-2}$ measured by first pressure sensing device 107a and second pressure sensing device 107b. In one scenario, main stream 101 could have on occasion one of many known chemicals passing through it at any time (in this example, chemical A, chemical B or chemical C). However, at any point in time, what chemical is passing through is not readily or immediately knowable by a system operator. Such pressure differential can determine in real-time what is passing through main stream 101. As all chemicals are known, an operator can know the viscosity of chemical A, the viscosity of chemical B, and the viscosity of chemical C, referred to as $V_A$, $V_B$, and $V_C$, respectively. Assuming $V_A > V_B > V_C$, operator can create VDPD system 100 with three pilot streams, first pilot stream 103a, second pilot stream 103b, and a third pilot stream 103c. In one embodiment, operator can adjust VDPD system 100 such that $V_C < V_C < V_{0-2} V_B < V_{0-1} < V_A$, wherein $V_{0-2}$ is the zero pressure differential viscosity between first stream 103a and second stream 103b, and $V_{0-1}$ is the zero pressure differential viscosity between first stream 103a and third stream 103c. In such system, chemical A will yield a positive differential pressure relative to both $V_{0-1}$ and $V_{0-2}$. Chemical B will yield a positive pressure differential to $V_{0-2}$, but will yield a negative differential pressure to $V_{0-1}$. Chemical C will yield a negative pressure to both $V_{0-1}$ and $V_{0-2}$. VDPD system 100 as it flows through main stream 101, and chemical B will yield a negative differential pressure in VDPD system 100 as it flows through main stream 101.

Further pilot stream 103 can be split into two or more pilot streams. One or more split pilot streams 106 can be reversed depending on the arrangement of viscosity and independent flow paths thus can cause the pressure to have an opposite reaction to viscosity. Further, the pressure differential in junction 104 can be relative to the viscosity of the fluid flowing through a flow path. In one embodiment, one or more pressure differential sensor can be used in split pilot streams 106. As such, pressure differential sensor can be placed in different areas of pilot stream for longer calibration and to achieve higher accuracy on pressure reading VDPD system 100 can further comprise an actuator. The pressure differential and/or the ratio of pressure differential to total pressure loss can be used either mechanically or through an electronic controller to move affect a control, such as by moving an actuator for VDPD system 100. As such VDPD system 100 can be used to control fluid stream in mainstream 101. Further, mainstream 101 can be opened or closed depending on the fluid viscosity, and the fluid phase Various changes in the details of the illustrated operational methods are possible without departing from the scope of the following claims. Some embodiments may combine the activities described herein as being separate steps. Similarly, one or more of the described steps may be omitted, depending upon the specific operational environment the method is being implemented in. It is to be understood that the above description is intended to be illustrative, and not restrictive. For example, the above-described embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein."

What is claimed is:

1. A viscosity dependent pressure differential system comprising
 a first pilot stream connectable to a main stream, said first pilot stream comprising
   a first inlet connected to said main stream;
   a first section comprising a first predominate pressure loss characteristic, connected to said first inlet;
   a first junction connected to said first section;
   a second section comprising a first predominate pressure loss characteristic, connected to said first junction; and
   a first outlet that connects said second section and to said main stream;
 a second pilot stream connectable to a main stream, said second pilot stream comprising
   a second inlet connected to said main stream;
   a third section comprising a third predominate pressure loss characteristic, connected to said tinlet;
   a second junction connected to said third section;
   a fourth section comprising a fourth predominate pressure loss characteristic, connected to said third junction; and
   a second outlet that connects said second section and to said main stream; and
 a pressure sensing device connecting that reads a differential pressure across said first junction and said second junction.

2. The system of claim 1 wherein said second inlet is said first inlet.

3. The system of claim 1 wherein said first predominant pressure loss characteristic and said fourth predominant pressure loss characteristic are frictional losses.

4. The system of claim 1 wherein said first predominant pressure loss characteristic and said fourth predominant pressure loss characteristic are inertial losses.

5. The system of claim 1 further comprising
 a third pilot stream connectable to a main stream, said third pilot stream comprising
   a third inlet connected to said main stream;
   a fifth section comprising a fifth predominate pressure loss characteristic, connected to said third inlet;
   a third junction connected to said fifth section;
   a sixth section comprising a sixth predominate pressure loss characteristic, connected to said third junction; and
   a third outlet that connects said second section and to said main stream.

6. A method of measuring a differential pressure, comprising
 measuring a differential pressure between a first junction and a second junction, said first junction between a first pilot stream first section having a first predominant pressure loss characteristic, and a second section having a second predominant pressure loss characteristic, said second junction between a second pilot stream first section having a third predominant pressure loss characteristic and a second pilot stream second section having a fourth predominant pressure loss characteristic.

7. The method of claim 6 wherein said first predominant pressure loss characteristic and said fourth predominant pressure loss characteristic are frictional losses.

8. The method of claim 6 comprising the additional step of determining a relative viscosity between a first fluid and a second fluid based on said differential pressure.

9. The method of claim 6 wherein said first predominant pressure loss characteristic and said fourth predominant pressure loss characteristic are inertial losses.

10. The method of claim 9 wherein said second predominant pressure loss characteristic and said third predominant pressure loss characteristic are frictional losses.

11. The method of claim 6 comprising the additional step of controlling a process depending on the value of said differential pressure.

12. The method of claim 11 wherein controlling said process comprises actuating a valve.

* * * * *